(12) United States Patent
Yen

(10) Patent No.: US 9,048,437 B2
(45) Date of Patent: *Jun. 2, 2015

(54) ORGANIC COMPOUND FOR ORGANIC ELECTROLUMINESCENT DEVICE

(71) Applicant: LUMINESCENCE TECHNOLOGY CORPORATION, Hsin-Chu (TW)

(72) Inventor: Feng-Wen Yen, Hsin-Chu (TW)

( * ) Notice: Subject to any disclaimer, the term of this patent is extended or adjusted under 35 U.S.C. 154(b) by 346 days.

This patent is subject to a terminal disclaimer.

(21) Appl. No.: 13/752,416

(22) Filed: Jan. 29, 2013

(65) Prior Publication Data

US 2014/0209866 A1 Jul. 31, 2014

(51) Int. Cl.
*H01L 51/50* (2006.01)
*C07D 471/04* (2006.01)
*C07D 221/18* (2006.01)
(Continued)

(52) U.S. Cl.
CPC ........ *H01L 51/0068* (2013.01); *H01L 51/0058* (2013.01); *H01L 51/0065* (2013.01); *H01L 51/0067* (2013.01); *H01L 51/52* (2013.01); *C09K 11/06* (2013.01); *C07C 13/62* (2013.01);
(Continued)

(58) Field of Classification Search
CPC ............ H01L 51/0058; H01L 51/0065; H01L 51/0067; H01L 51/0068; H01L 51/52; H01L 2251/308; H01L 51/54; H01L 51/0072; H01L 51/5012; C07C 13/62; C07C 13/64; C07C 2103/18; C07C 2103/90; C07C 2103/24; C07D 221/18; C09K 11/06; C09K 2211/1011; C09K 2211/1029; H05B 33/14
See application file for complete search history.

(56) References Cited

U.S. PATENT DOCUMENTS 5,935,721 A 8/1999 Shi et al.
7,691,492 B2 4/2010 Yamada et al.
(Continued)

FOREIGN PATENT DOCUMENTS

WO 2006130598 7/2006
WO WO 2006/130598 * 12/2006
(Continued)

*Primary Examiner* — Dawn Garrett

(57) ABSTRACT

The present invention discloses a novel organic compound is represented by the following formula(A), the organic EL device employing the compound as blue emitting layer can lower driving voltage, prolong half-lifetime and increase the efficiency.

Formula (A)

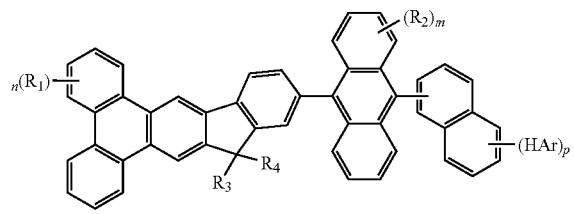

Wherein m represent an integer of 0 to 8, n represent an integer of 0 to 10, p represent an integer of 0 to 7, HAr represent a hydrogen, a halide, a cyanine group, a substituted or unsusbstituted heteroaryl group system having 5 to 6 aromatic ring atoms, $R_1$ to $R_4$ are identical or different. $R_1$ to $R_4$ are independently selected from the group consisting of a hydrogen atom, alkyl group having 1 to 30 carbon atoms, a substituted or unsubstituted aryl group having 6 to 30 carbon atoms, a substituted or unsubstituted aralkyl group having 6 to 30 carbon atoms.

6 Claims, 1 Drawing Sheet

12 — metal electrode
11 — electron injection layer
10 — electron transport layer
9 — emitting layer
8 — hole transport layer
7 — hole injection layer
6 — transparent electrode

(51) Int. Cl.
*C07C 13/62* (2006.01)
*H01L 51/00* (2006.01)
*H01L 51/52* (2006.01)
*C09K 11/06* (2006.01)

(52) U.S. Cl.
CPC ......... *C07C 2103/24* (2013.01); *C07C 2103/90* (2013.01); *C07D 221/18* (2013.01)

(56) References Cited

U.S. PATENT DOCUMENTS

| | | |
|---|---|---|
| 7,839,074 B2 | 11/2010 | Ikeda et al. |
| 7,985,491 B2 | 7/2011 | Kubota et al. |
| 2004/0076853 A1 | 4/2004 | Jarikov |
| 2011/0073845 A1* | 3/2011 | Tseng et al. .............. 257/40 |
| 2014/0131664 A1* | 5/2014 | Yen et al. ................ 257/40 |
| 2014/0175383 A1* | 6/2014 | Yen et al. ................ 257/40 |
| 2014/0175384 A1* | 6/2014 | Yen et al. ................ 257/40 |

FOREIGN PATENT DOCUMENTS

| | | |
|---|---|---|
| WO | 2012035962 | 3/2012 |
| WO | WO 2012/035962 * | 3/2012 |

* cited by examiner

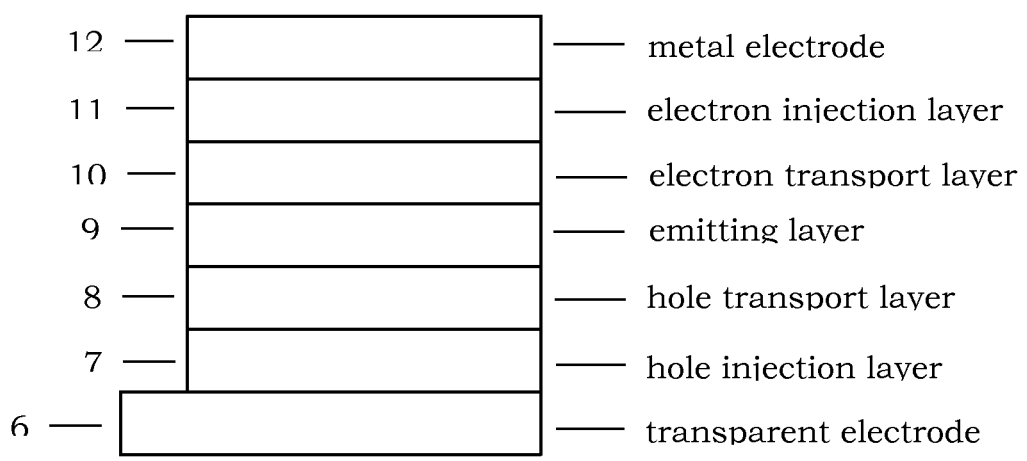

ORGANIC COMPOUND FOR ORGANIC ELECTROLUMINESCENT DEVICE

FIELD OF INVENTION

The present invention generally relates to a novel compound and organic electroluminescent (herein referred to as organic EL) device using the compound. More specifically, the present invention relates to the compound having general formula(A), an organic EL device employing the compound as fluorescent blue emitting layer.

BACKGROUND OF THE INVENTION

Organic EL device has many advantages such as self-emitting, wider viewing angles, faster response speeds and highly luminescence. Their simpler fabrication and capable of giving clear display comparable with LCD, making organic EL device an industry display of choice. Organic EL device contain emitting materials which are arranged between a cathode and a anode, when a applied driving voltage is added, an electron and a hole were injected into the emitting layer and recombined to form an exciton. The exciton which results from an electron and a hole recombination have a singlet spin state or triplet spin state. Luminescence from a singlet spin state emits fluorescence and luminescence from triplet spin state emits phosphorescence.

Organic EL device are generally composed of functionally divided organic multi-layers, e.g., hole injection layer (HIL), hole transporting layer (HTL), emitting layer (EML), electron transporting layer (ETL) and electron injection layer (EIL) and so on. A emitting material have good charge carrier mobility and excellent operational durability can lower driving voltage and power consumption, increasing efficiency and half-lifetime of organic EL device.

For full-colored flat panel displays in AMOLED, the compound used for the blue emitting layer are still unsatisfactory in half-lifetime and driving voltage. Many compounds are used for fluorescent blue host in emitting layer. U.S. Pat. No. 5,935,721 used 9,10-di(naphthalen-2-yl) anthracene (AND) as blue host in emitting layer. U.S. Pat. No. 7,691,492 used 1,1-(9,9-dimethyl-9H-fluorene-2,7-diyl)dipyrene (DFDP) as host for blue organic EL device. These compounds still have disadvantages for industrial practice use.

In the present invention, for the purpose to prolong the half-life time and lower driving voltage for fluorescent blue emitting organic EL device, we employ an indenotriphenylene skeleton link to a heteroaryl group substituted naphthyl anthracene group to finish the compound represented as general formula(A). The triphenylene skeleton show good thermal stability and charge carrier mobility for organic EL device. Triphenylene skeleton based derivative disclosed in U.S. Patent No. 2004/0076853, WO2006/130598 and WO2012035962A1 are used for organic EL device are described. There are no prior arts demonstrate such an indenotriphenylene skeleton formula(A) used as fluorescent blue host for organic EL device.

SUMMARY OF THE INVENTION

In accordance with the present invention, the compound and their use as emitting material for organic EL device are provided. The compound can overcome the drawbacks of the conventional material like as shorter half-life time, higher driving voltage and power consumption, especially for blue fluorescent emitting compound in the present invention. For full-colored flat panel displays, the blue emitting material is still not satisfied for practice use for its shorter half-life time and higher driving voltage.

An object of the present invention is to provide the compound which can be used as emitting material for organic EL device.

Another object of the present invention is to apply the material for fluorescent blue emitting material of organic EL device and improve the half-lifetime, lower driving voltage, lower power consumption.

The present invention has the economic advantages for industrial practice. Accordingly, the present invention discloses the compound which can be used for organic EL device is disclosed. The mentioned compound is represented by the following formula(A):

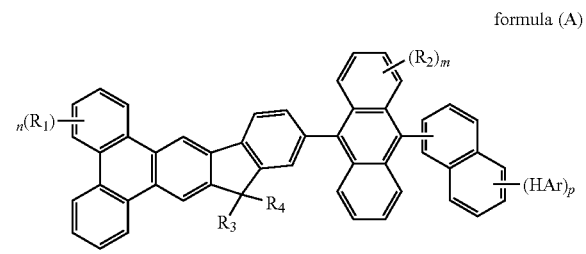

formula (A)

Wherein m represent an integer of 0 to 8, n represent an integer of 0 to 10, p represent an integer of 0 to 7, HAr represent a hydrogen, a halide, a cyanine group, a substituted or unsusbstituted heteroaryl group system having 5 to 6 aromatic ring atoms, $R_1$ to $R_4$ are identical or different. $R_1$ to $R_4$ are independently selected from the group consisting of a hydrogen atom, alkyl group having 1 to 30 carbon atoms, a substituted or unsubstituted aryl group having 6 to 30 carbon atoms, a substituted or unsubstituted aralkyl group having 6 to 30 carbon atoms.

BRIEF DESCRIPTION OF THE DRAWINGS

FIG. 1 show one example of organic EL device in the present invention. 6 is transparent electrode, 12 is metal electrode, 7 is hole injection layer which is deposited onto 6, 8 is hole transporting layer which is deposited onto 7, 9 is fluorescent emitting layer which is deposited onto 8, 10 is electron transporting layer which is deposited onto 9, 11 is electron injection layer which is deposited onto 10.

DESCRIPTION OF THE PREFERRED EMBODIMENTS

What probed into the invention is the compound and organic EL device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodi-

DEFINITION

In a first embodiment of the present invention, the compound which can be used as fluorescent blue emitting material of organic EL device are disclosed. The mentioned compound are represented by the following formula(A):

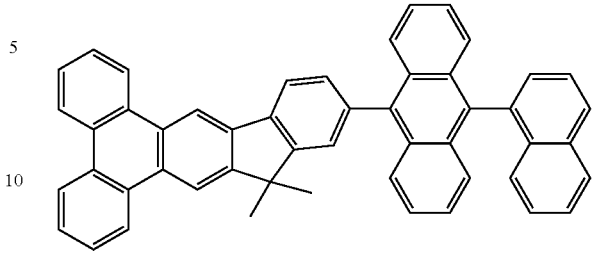

formula (A)

Wherein m represent an integer of 0 to 8, n represent an integer of 0 to 10, p represent an integer of 0 to 7, HAr represent a hydrogen, a halide, a cyanine group, a substituted or unsusbstituted heteroaryl group system having 5 to 6 aromatic ring atoms, $R_1$ to $R_4$ are identical or different. $R_1$ to $R_4$ are independently selected from the group consisting of a hydrogen atom, alkyl group having 1 to 30 carbon atoms, a substituted or unsubstituted aryl group having 6 to 30 carbon atoms, a substituted or unsubstituted aralkyl group having 6 to 30 carbon atoms.

According to the formula(A), preferable HAr represented by the group like fluorine atom, pyridyl group, pyrrolyl group, imidazolyl group, pyrazinyl group, furyl group, thiophene group, 1,3,5-triazinyl group, preferable $R_1$ to $R_4$ represented by the group like hydrogen, bromide, methyl group, ethyl group, propyl group, isopropyl group, butyl group, tert-butyl group, phenyl group, 1-biphenyl group, 2-biphenyl group, 3-biphenyl group, 1-naphthalene group, 2-naphthalene group.

In this embodiment, some materials are shown below:

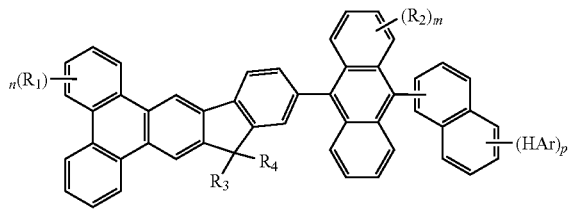

-continued

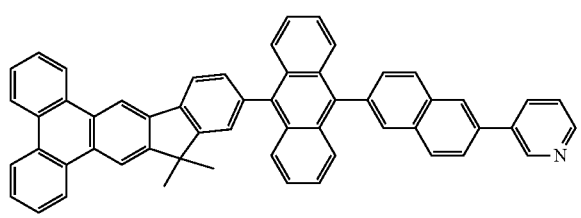
A-9

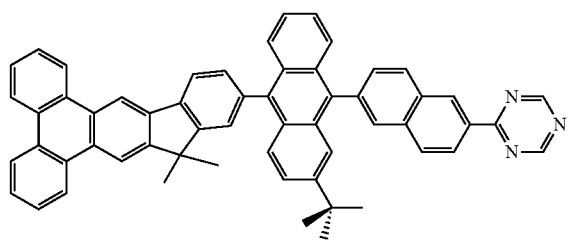
A-10

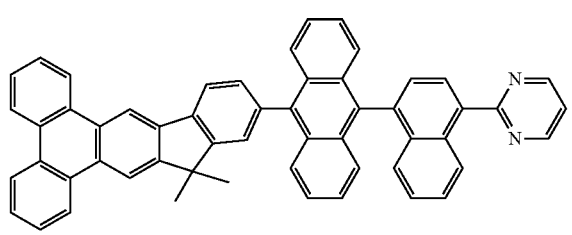
A-11

Detailed preparation for formula(A) could be clarified by exemplary embodiments, but the present invention is not limited to exemplary embodiments.

EXAMPLE 1

Synthesis of Compound A-1

Synthesis of 4-fluoronaphthalen-1-ylboronic acid

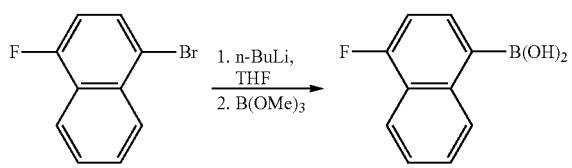 [SMILES: Fc1ccc(Br)c2ccccc12 ; OB(O)c1ccc(F)c2ccccc12 ; "THF"]

A three-necked 250 mL flask fitted with two dropping funnels, magnetic stirring bar, and low-temperature thermometer was charged with 2-bromo-4fluoronaphthalene (10.9 g, 48.3 mmol) under nitrogen. Dry THF (100 mL) was added, and the solution was cooled to −78° C. To this solution was added n-butyllithium (33.2 mL of a 1.6 M solution, 53.1 mmol) dropwise through the first dropping funnel. The solution was stirred at −78° C. for 2 h whereupon trimethyl borate (6.0 g, 57.9 mmol) dissolved in 10 mL of dry THF was added dropwise through the second dropping funnel. The solution was allowed to warm to room temperature overnight. The reaction was quenched with dilute HCl (20%, 70 mL), and the reaction mixture was concentrated at 30° C. to 50% of its original volume by rotary evaporation and poured into H$_2$O. The resulted biphasic solution was extracted with ethyl acetate (2×100 mL). The organic phases solution were washed twice with H$_2$O and concentrated by rotary evaporation. The crude 4-fluoronaphthalen-1-ylboronic acid product was collected as a white solid powder by filtration and washed with hexane several times to remove impurity. It was dried at 20° C. under vacuum and used without further purification. It gave a white solid product in 78% yield (7.04 g, 37.7 mmol).

Synthesis of 9-bromo-10-(4-fluoronaphthalen-1-yl)anthracene

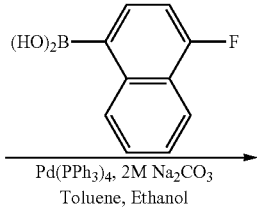

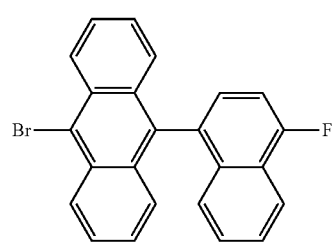

A three-necked 500 mL flask was charged with 9,10-Dibromo anthrancene (12.7 g, 37.7 mmol), 4-fluoronaphthalen-1-yl boronic acid (7.03 g, 37.7 mmol), Pd(PPh$_3$)$_4$ (0.87 g, 0.75 mmol), aqueous Na$_2$CO$_3$ (2.0 M, 41.6 mL, 83.1 mmol), ethanol (42 mL), and toluene (100 mL). The mixture was degassed and refluxed for 24 h under a nitrogen atmosphere. After being cooled, the solvent was evaporated under vacuum and the product was extracted with dichloromethane (2×200 mL). The CH$_2$Cl$_2$ solution was washed with water and dried with MgSO$_4$. Evaporation of the solvent, followed by column chromatography on silica gel, gives a yellow product in 80% yield (12.14 g, 30.2 mmol).

Synthesis of 2-(biphenyl-2-yl)-7-bromo-9,9-dimethyl-9H-fluorene

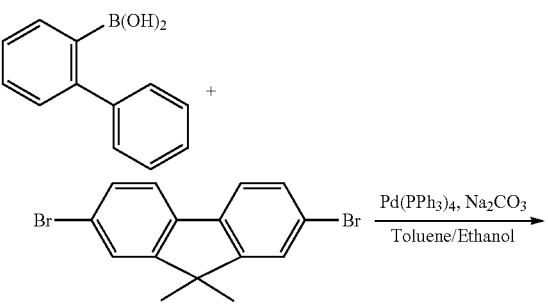

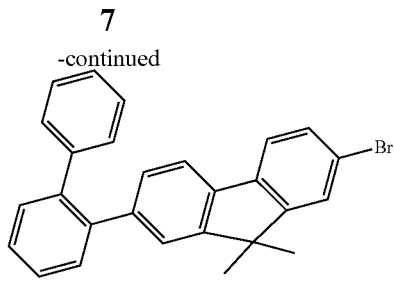

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of tetrakis(triphenylphosphine) palladium, 75 ml of 2M $Na_2CO_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica(hexane-dichloromethane) to give product (26.8 g, 63.0 mmol, 63%) as a white solid. $^1$H NMR ($CDCl_3$, 400 MHz): chemical shift (ppm) 7.61 (d, J=7.8 Hz, 1H), 7.55~7.53 (m, 2H), 7.49~7.42 (m, 5H), 7.29 (d, J=8.0 Hz, 1H), 7.20~7.14 (m, 5H), 6.98 (s, 1H), 1.21 (s, 6H)

Synthesis of 12-bromo-10,10-dimethyl-10H-indeno[1,2-b]triphenylene

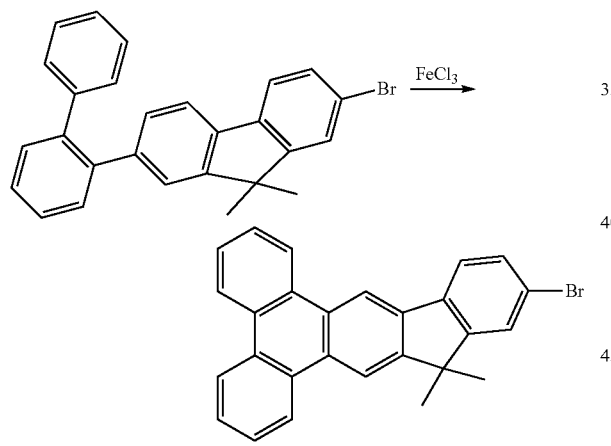

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron (III) chloride was then added, and the mixture was stirred one hour. Methanol 500 ml were added to the mixture and the organic layer was separated and the solvent removed in vacuo. The residue was purified by column chromatography on silica(hexane-dichloromethane) afforded a white solid (10.7 g, 25.3 mmol, 40%). $^1$H NMR ($CDCl_3$, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[1,2-b]triphenylen-12-yl)-4,4,5,5-tetramethyl-1,3,2-dioxaborolane

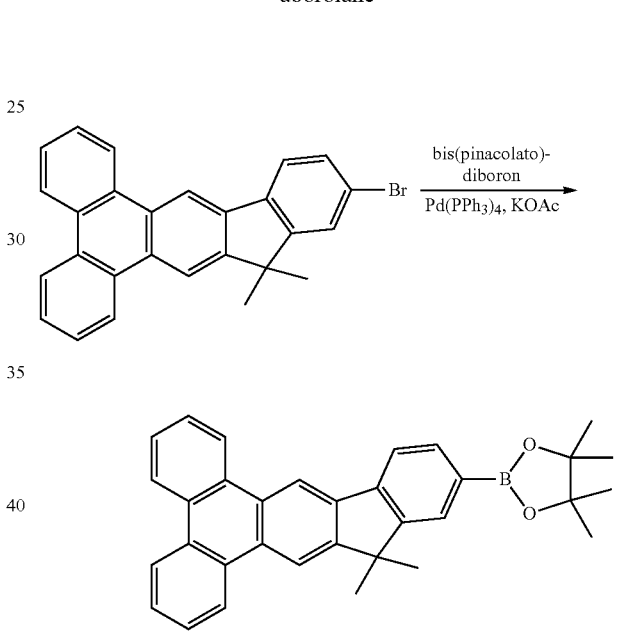

Synthesis of 10,10-dimethyl-12-(10-(naphthalen-2-yl)anthracen-9-yl)-10H-indeno[1,2-b]triphenylene

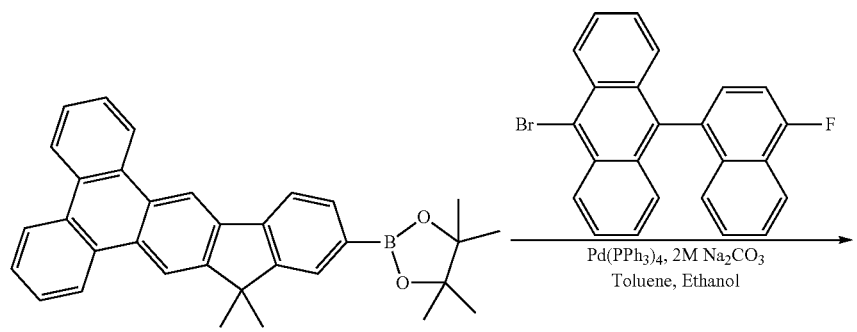

-continued

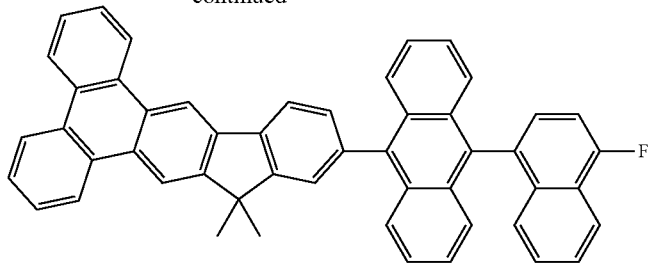

A three-necked 250 mL flask was charged with 2-(10,10-dimethyl-10H-indeno[1,2-b]triphenylen-12-yl)-4,4,5,5-tetramethyl-1,3,2-dioxaborolane (5.0 g, 10.6 mmol), 9-bromo-10-(4-fluoronaphthalen-1-yl) anthracene (4.26 g, 10.6 mmol), Pd(PPh$_3$)$_4$ (0.25 g, 0.21 mmol), aqueous Na$_2$CO$_3$ (2.0 M, 12 mL, 23.4 mmol), ethanol (15 mL), and toluene (50 mL). The mixture was degassed and refluxed for 24 h under a nitrogen atmosphere. After being cooled, H$_2$O (50 mL) was added to the mixture. The crude product was collected as a yellow-green solid powder by filtration and washed with methanol several times to remove impurity. It was dried at 20° C. under vacuum and gave a bright yellow-green solid product in 85% yield (6.01 g, 9.0 mmol). MS (m/z, FAB$^+$): 664.8 $^1$H NMR (CDCl$_3$, 400 MHz): chemical shift (ppm) 9.14 (s, 1H), 8.90 (d, J=7.80 Hz, 1H), 8.82 (d, J=7.92 Hz, 1H), 8.79 (s, 1H), 8.73 (d, J=7.88 Hz, 2H), 8.23 (d, J=7.72 Hz, 1H), 8.11 (d, J=8.24 Hz, 1H), 8.07~8.02 (m, 2H), 7.96 (d, J=7.40 Hz, 1H), 7.89 (d, J=8.64 Hz, 2H), 7.78~7.59 (m, 9H), 7.42~7.28 (m, 4H), 7.20 (d, J=7.40 Hz, 1H), 1.76 (s, 6H).

EXAMPLE 2 TO EXAMPLE 4

Synthesis of Compound A-2 to A-4

The synthesis of procedures are the same process with EXAMPLE 1, the product yield (%) of the final step are individually 75.6% for Compound A-2, 89.8% for compound A-3 and 46.5% for A-4.

EXAMPLE 5

Synthesis of Compound A-5

Synthesis of 2-(4-bromonaphthalen-1-yl)thiophene

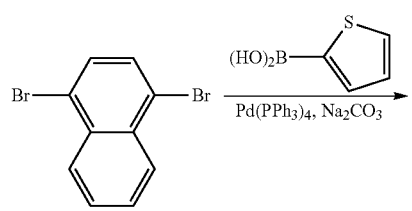

-continued

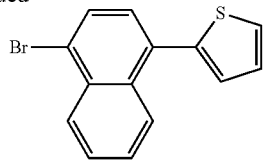

A mixture of 28.6 g (100 mmol) of 1,4-dibromonaphthalene, 15.35 g (120 mmol) of thiophen-2-ylboronic acid, 2.31 g (2 mmol) of tetrakis(triphenyl phosphine)palladium, 75 ml of 2M Na$_2$CO$_3$, 150 ml of EtOH and 300 ml toluene was degassed and placed under nitrogen, and then heated at 100° C. for 4 h. After finishing the reaction, the mixture was allowed to cool to room temperature. The organic layer was extracted with ethyl acetate and water, dried with anhydrous magnesium sulfate, the solvent was removed and the residue was purified by column chromatography on silica(hexane-dichloromethane) to give product (21.1 g, 73 mmol, 73%) as a white solid.

Synthesis of 4,4,5,5-tetramethyl-2-(4-(thiophen-2-yl) naphthalene-1-yl)-1,3,2-dioxaborolane

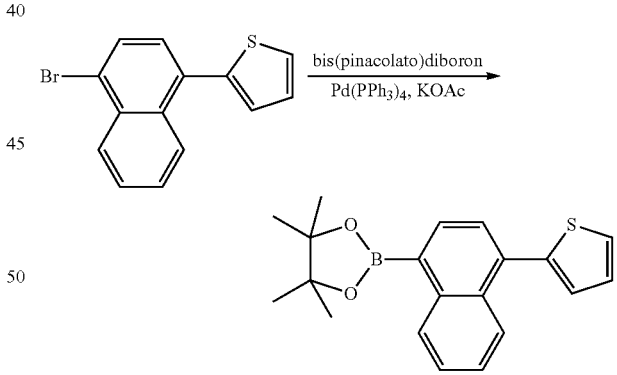

A mixture of 21.1 g (73 mmol) of 2-(4-bromonaphthalen-1-yl)thiophene, 24.1 g (95 mmol) of bis(pinacolato)diboron, 1.7 g (1.46 mmol) of tetrakis(triphenylphosphine)palladium, 14.3 g (146 mmol) of potassium acetate, and 600 ml 1,4 dioxane was degassed and placed under nitrogen, and then heated at 90° C. for 6 h. After finishing the reaction, the mixture was allowed to cool to room temperature. The organic phase separated and washed with ethyl acetate and water. After drying over magnesium sulfate, the solvent was removed in vacuum. The residue was purified by column chromatography on silica(hexane-dichloromethane) to give product (20.1 g, 60 mmol, 82%)

Synthesis of 2-(4-(10-bromoanthracen-9-yl)naphthalen-1-yl)thiophene

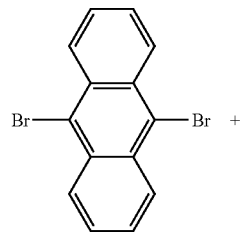

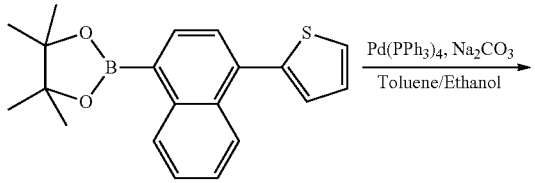

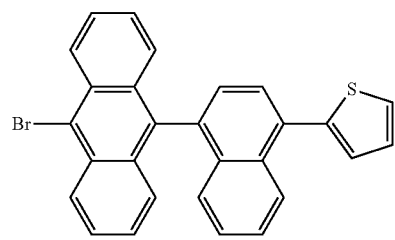

A mixture of 13.4 g (40 mmol) of 9,10-dibromoanthracene, 20.1 g (60 mmol) of 4,4,5,5-tetramethyl-2-(4-(thiophen-2-yl)naphthalen-1-yl)-1,3,2-dioxaborolane, 0.46 g (0.4 mmol) of tetrakis(triphenylphosphine)palladium, 30 ml of 2M $Na_2CO_3$, 80 ml of EtOH and 160 ml toluene was degassed and placed under nitrogen, and then heated at 90° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica(hexane-dichloromethane) to give product 9.9 g (53%) as a yellow solid.

Synthesis of 2-(4-(10-(10,10-dimethyl-10H-indeno[2,1-b]triphenylen-12-yl)anthracen-9-yl)naphthalen-1-yl)thiophene

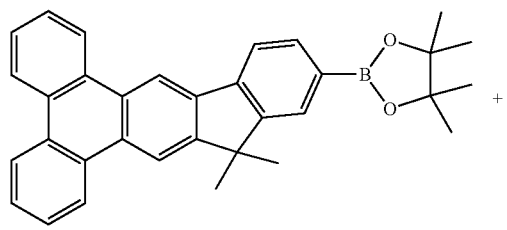

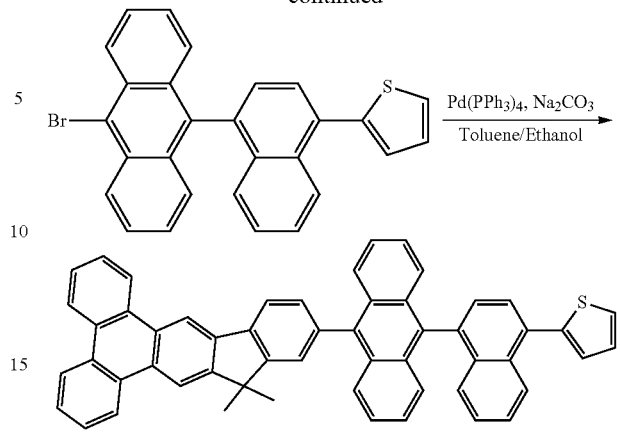

A mixture of 6.5 g (14 mmol) of 2-(4-(10-bromoanthracen-9-yl)naphthalene-1-yl)thiophene, 7.53 g (16 mmol) of 2-(10,10-dimethyl-10H-indeno[1,2-b]triphenylen-12-yl)-4,4,5,5-tetramethyl-1,3,2-dioxaborolane, 0.16 g (0.14 mmol) of tetrakis(triphenylphosphine)palladium, 11 ml of 2M $Na_2CO_3$, 30 ml of EtOH and 65 ml toluene was degassed and placed under nitrogen, and then heated at 90° C. for 4 h. After finishing the reaction, the mixture was allowed to cool to room temperature. Than 500 ml MeOH was added, while stirring and the precipitated product was filtered off with suction. To give 6.4 g (yield 63%) of yellow product which was recrystallized from toluene. MS (m/z, $FAB^+$): 728.1; $^1$H NMR ($CDCl_3$, 400 MHz): chemical shift (ppm) 9.13 (s, 1H), 8.64~8.56 (m, 3H), 8.31~8.05 (m, 5H), 7.95~7.83 (m, 9H), 7.68~7.61 (m, 2H), 7.55 (d, J=8.00 Hz, 1H), 7.49~7.40 (m, 6H), 7.18 (d, J=6.20 Hz, 1H), 7.02 (t, J=6.20 Hz, 1H), 6.55 (d, J=8.00 Hz, 1H), 1.81 (s, 6H).

EXAMPLE 6 TO EXAMPLE 11

Synthesis of Compound A-6 to A-11

The synthesis of procedures are the same process with EXAMPLES, the product yield (%) of the final step are individually 56.8% for Compound A-6, 51.5% for compound A-7, 65.1% for Compound A-8, 43.38% for compound A-9, 35.6% for Compound A-10 and 36.5% for A-11.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a guest material. This is achieved by co-vaporization from two or more sources.

Dipyrazino[2,3-f2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine(NPB) is most widely used as the hole transporting layer and 2,9-bis(naphthalene-2-yl)-4,7-diphenyl-1,10-phenanthroline (NBphen) is used as electron transporting material in organic EL device for its high thermal stability and long life-time than BPhen/BCP. 9,10-di(naphthalen-2-yl)anthracene (AND, U.S. Pat. No. 5,935,721), 1,1-(9,9-dimethyl-9H-fluorene-2,7-diyl)dipyrene (DFDP, U.S. Pat. No. 7,691,492) and 9-(4-(naphthalen-1-yl)phenyl)-10-(naphthalen-2-yl)anthracene (H1, U.S. Pat. No. 7,839,074) are used as emitting host for comparative example, and (E)-6-(4-(diphenylamino)styryl)-N,N-diphenyl naphthalen-2-amine (D1) is used as guest. The above organic EL materials for producing standard organic EL device in this invention shown its chemical structure as following:

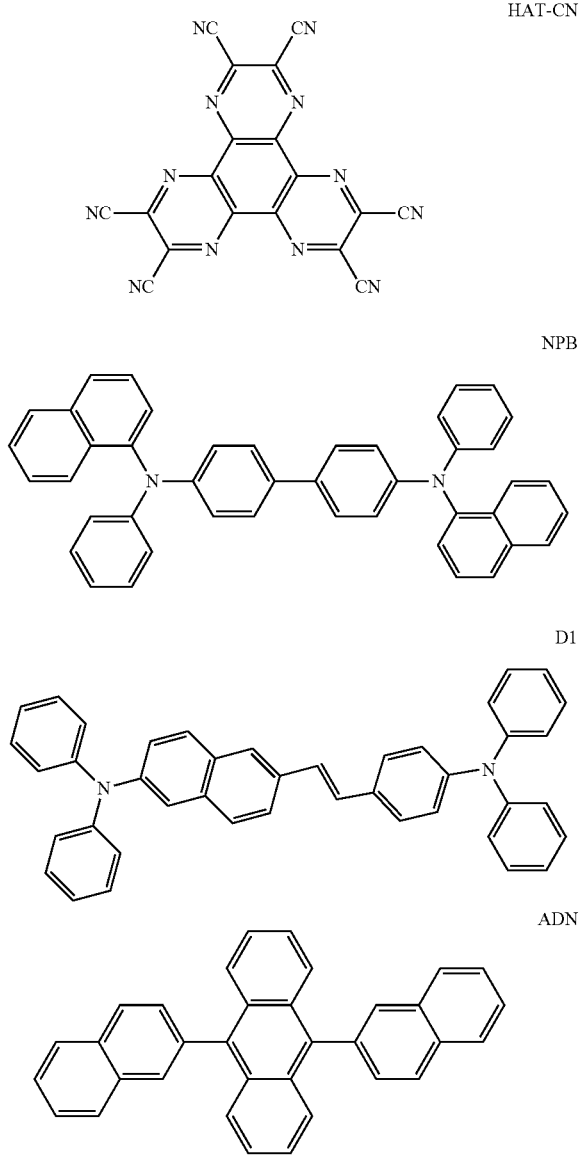

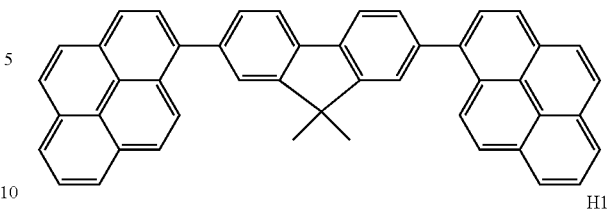

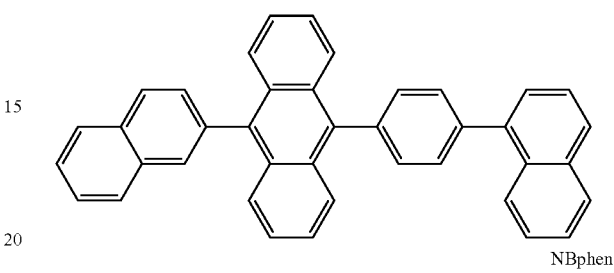

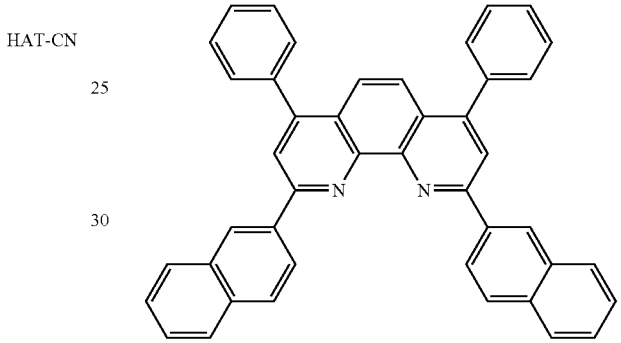

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 12

Using a procedure analogous to the above mentioned general method, fluorescent blue-emitting organic EL device having the following device structure were produced (See FIG. 1): ITO/HAT-CN (20 nm)/NPB (60 nm)/fluorescent blue host doped 5% DPASN (35 nm)/NPhen (30 nm)/LiF (0.5 nm)/Al (160 nm). The I-V-B and half-life time of fluorescent blue-emitting OLED device testing report as Table 1, The half-life time is defined that the initial luminance of 1000 $cd/m^2$ has dropped to half.

TABLE 1

| Fluorescent blue host | Voltage (V) | Luminance (cd/m$^2$) | Yield (cd/A) | CIE (y) | Half-lifetime (hour) Initial luminance = 1000 (cd/m$^2$) |
|---|---|---|---|---|---|
| Compound A1 | 5.0 | 1000 | 6.2 | 0.172 | 580 |
| Compound A2 | 5.3 | 1000 | 6.0 | 0.178 | 560 |
| Compound A3 | 4.8 | 1000 | 6.4 | 0.180 | 680 |
| Compound A4 | 5.2 | 1000 | 6.1 | 0.185 | 600 |
| Compound A5 | 4.8 | 1000 | 7.1 | 0.182 | 420 |
| Compound A6 | 4.5 | 1000 | 7.3 | 0.179 | 400 |
| Compound A9 | 7.0 | 1000 | 5.8 | 0.189 | 250 |
| Compound A10 | 7.2 | 1000 | 5.3 | 0.182 | 280 |
| ADN | 8.5 | 1000 | 2.2 | 0.142 | 120 |
| DFDP | 7.5 | 1000 | 3.1 | 0.188 | 200 |
| H1 | 6.0 | 1000 | 6.8 | 0.168 | 420 |

In the above preferred embodiments, we show that the material formula(A) used as fluorescent blue host than comparable example AND, DFDP and H1 with higher half-life time and practical operation durability. Under the same Luminance (cd/m$^2$), lower driving voltage than comparable example AND, DFDP and H1 has also been achieved at 1000 cd/m$^2$ using the mentioned material formula(A) for blue-emitting organic EL devices. The efficiency of all present invention examples also show over 5.0 cd/A and better than comparable example AND and DFDP. The present invention formula(A) can be used as fluorescent blue host.

To sum up, the present invention discloses a organic compound which can be used for organic EL device is disclosed. The mentioned compound are represented by the following formula(A):

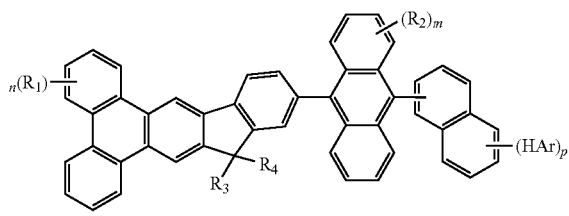

Formula (A)

Wherein m represent an integer of 0 to 8, n represent an integer of 0 to 10, p represent an integer of 0 to 7, HAr represent a hydrogen, a halide, a cyanine group, a substituted or unsusbstituted heteroaryl group system having 5 to 6 aromatic ring atoms, R$_1$ to R$_4$ are identical or different. R$_1$ to R$_4$ are independently selected from the group consisting of a hydrogen atom, alkyl group having 1 to 30 carbon atoms, a substituted or unsubstituted aryl group having 6 to 30 carbon atoms, a substituted or unsubstituted aralkyl group having 6 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An organic EL compound with a general formula(A) as follows:

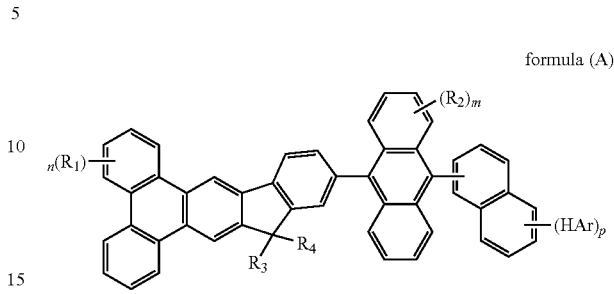

formula (A)

wherein m represents an integer of 0 to 8, n represents an integer of 0 to 10, p represents an integer of 0 to 7, HAr represents a hydrogen, a halide, a cyanine group, or a substituted or unsubstituted heteroaryl group system having 5 to 6 aromatic ring atoms; R$_1$ to R$_4$ are identical or different, R$_1$ to R$_4$ are independently selected from the group consisting of a hydrogen atom, alkyl group having 1 to 30 carbon atoms, a substituted or unsubstituted aryl group having 6 to 30 carbon atoms, and a substituted or unsubstituted aralkyl group having 6 to 30 carbon atoms.

2. An organic EL compound according to claim 1, wherein HAr is represented by the group consisting of fluorine atom, pyridyl group, pyrrolyl group, imidazolyl group, pyrazinyl group, furyl group, thiophene group, and 1,3,5-triazinyl group.

3. A organic EL device comprising a pair of electrodes consisting of a cathode and an anode and between the pairs of the electrodes comprising a layer of material with a general formula(A) as follows:

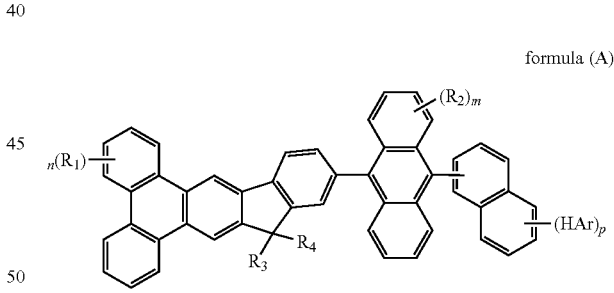

formula (A)

wherein m represents an integer of 0 to 8, n represents an integer of 0 to 10, p represents an integer of 0 to 7, HAr represent a hydrogen, a halide, a cyanine group, or a substituted or unsubstituted heteroaryl group system having 5 to 6 aromatic ring atoms; R$_1$ to R$_4$ are identical or different, R$_1$ to R$_4$ are independently selected from the group consisting of a hydrogen atom, alkyl group having 1 to 30 carbon atoms, a substituted or unsubstituted aryl group having 6 to 30 carbon atoms, and a substituted or unsubstituted aralkyl group having 6 to 30 carbon atoms.

4. An organic EL device according to claim 3, wherein the material according to general formula (A) is selected from the group consisting of:

A-1
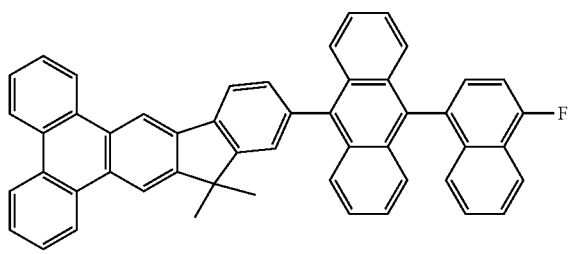
A-2
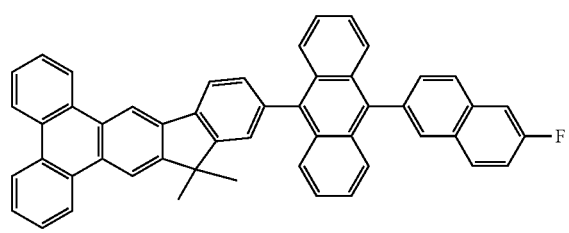
A-3
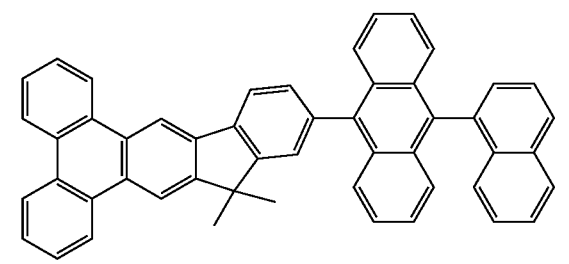
A-4
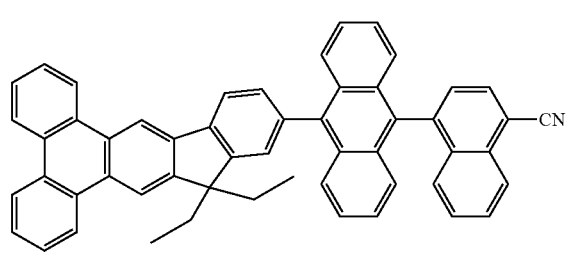
A-5
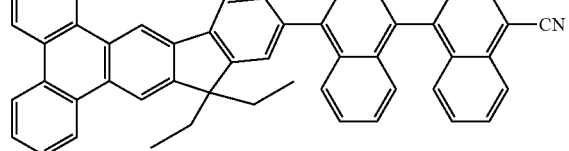
A-6
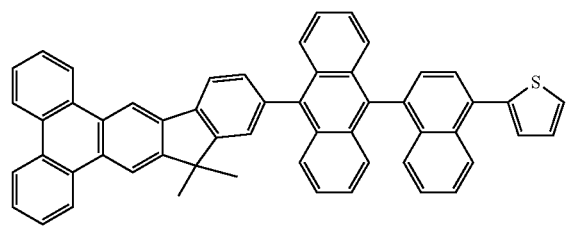
A-7
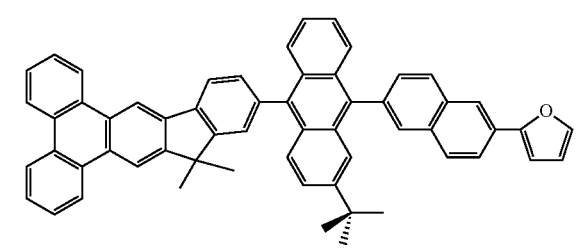
A-8
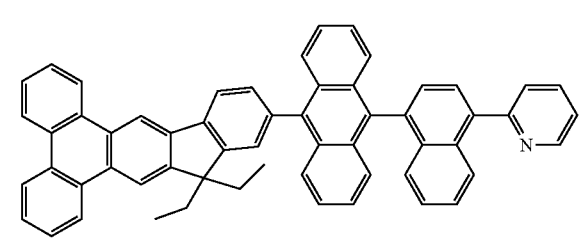
A-9
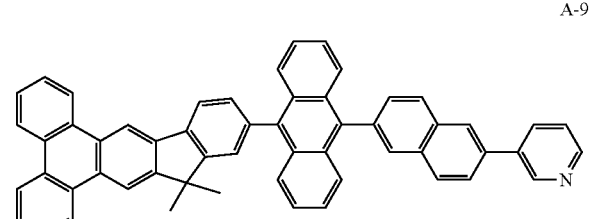
A-10
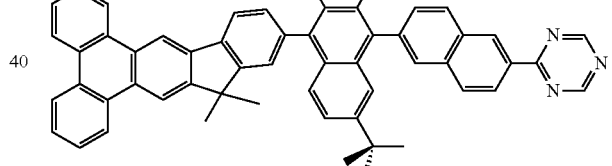
and
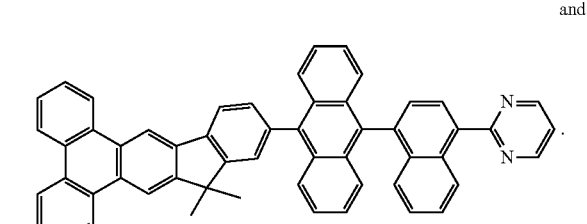
5. An organic EL device according to claim 3, wherein the material according to general formula (A) functions as a fluorescent emitting layer of the organic EL device.
6. An organic EL device according to claim 3, wherein the material according to general formula (A) functions as a fluorescent blue emitting host of the organic EL device.
* * * * *